US00PP17744P2

(12) United States Plant Patent
Hall

(10) Patent No.: US PP17,744 P2
(45) Date of Patent: May 22, 2007

(54) RASPBERRY PLANT NAMED 'MOUTERE'

(50) Latin Name: *Rubus idaeus*
Varietal Denomination: Moutere

(75) Inventor: Harvey K. Hall, Nelson (NZ)

(73) Assignee: The Horticulture and Food Research Institute of New Zealand, Limited, Auckland (NZ)

( * ) Notice: Subject to any disclaimer, the term of this patent is extended or adjusted under 35 U.S.C. 154(b) by 235 days.

(21) Appl. No.: 10/859,254

(22) Filed: Jun. 1, 2004

(51) Int. Cl.
*A01H 5/00* (2006.01)

(52) U.S. Cl. ..... Plt./204

(58) Field of Classification Search ..... Plt./204
See application file for complete search history.

*Primary Examiner*—Kent Bell
*Assistant Examiner*—Annette H Para
(74) *Attorney, Agent, or Firm*—Greenlee Winner and Sullivan PC

(57) ABSTRACT

A new and distinct floricane fruiting variety of red raspberry, named 'Moutere', botanically identified as *Rubus idaeus* L. is described. The new variety is distinguished from others by its early season high yields of attractive, uniform sized, large, bright red berries. The plant exhibits a semi spine-free upright growth habit, of strong vigor. The fruit are suitable for consumption as early season high-grade fresh berries and are very attractive when packaged for the fresh market. In addition, the plant has displayed resistance to Raspberry Bushy Dwarf Virus (RBDV) under New Zealand conditions.

8 Drawing Sheets

Genus and species of plant claimed: *Rubus idaeus.*

BACKGROUND TO THE INVENTION

The new variety of red raspberry, *Rubus idaeus* L., was created in the course of a planned breeding program carried out at HortResearch Nelson, New Zealand. The parents used to make the cross in 1987, were the cultivars Haida (seed parent) and Qualicum (pollen parent). Both of these parents originated in the Canada Agriculture breeding programme in British Columbia. The cross was made in British Columbia, Canada. Haida (Malling Promise×Creston) was an early release from the British Columbia raspberry breeding programme. It has had limited success as a cultivar in its own right, primarily as a cold hardy selection of Eastern Canada. Haida has also been recognised in New Zealand for its resistance to Raspberry Bushy Dwarf Virus (RBDV), low stature, short internode length and its low chill adaptation. Qualicum (Glen Moy×Chilliwack) is RBDV susceptible and has very vigorous canes and large attractive fruit which are good for fresh market and processing.

Seed from this cross was grown at HortResearch, Nelson, New Zealand and the original plant of the new variety was selected during the 1989–90 summer (Southern Hemisphere) and was found to exhibit:

(a) a semi spine-free upright growth habit of strong vigor, (b) the ability to form on floricanes attractive large red fruit of good flavor in high yields on medium-long fruiting trusses, that ripen early season, and (c) resistance to Raspberry Bushy Dwarf Virus (RBDV).

The new variety was first asexually propagated in 1991, being reproduced by vegetative cuttings arising from root cuttings. Cuttings developed this way in spring, root within a 3–4 week propagation period, and plants suitable for field planting are then ready in autumn of the same year. The resulting plants propagated true to type, demonstrating that the characteristics of the new variety are stable and are transmitted without change through succeeding generations.

SUMMARY OF THE INVENTION

The new variety was tested and evaluated during the years 1992 to 2001 at HortResearch Nelson, New Zealand and at Canada Agriculture in British Columbia, Canada.

When compared to the parent 'Haida', the new variety is found to form larger, similarly bright red fruit, in higher yields. 'Moutere' is further distinguished from 'Haida' by having canes that are thicker and longer, and producing fruit which are longer and more conical, with similar shininess and requiring less force to separate the berry from the plug.

When compared to the parent 'Qualicum', the new variety exhibits more compact, richer red colored and shinier fruit in similar yields, an earlier picking date (approximately 7 to 8 days earlier) and a similar picking period. 'Moutere' is further distinguished from 'Qualicum' by having lower cane vigor.

Data collected during the evaluation period comparing fruiting performance of the new variety with standard New Zealand varieties is presented in Table 1.

TABLE 1

Comparison of fruiting performance.

| Variety | Average Yield* (T/ha) | Berry Weight (g) |
|---|---|---|
| 'Moutere' | 20.9 | 4.6 |
| 'Marcy' | 21.1 | 2.8 |
| 'Skeena' | 15.8 | 3.3 |
| 'Chilliwack' | 15.0 | 2.9 |
| 'Waimea' | 22.3 | 3.3 |
| 'Tadmor' | 25.3 | 4.6 |
| 'Motueka' | 28.6 | 3.5 |

*Hand-picked

The data presented in Table 1. demonstrates the high fruit yield potential of the new variety. Berries of 'Moutere' showed an average weight of 4.6 g although fruit weight was observed to diminish later in the harvest season. Berries of the new variety are suitable for consumption as early season, high-grade fresh fruit.

TABLE 2

Comparison of seasonal performance in British Columbia

| Variety | Early Yield (%) 1999 | Early Yield (T/ha) 1999 | Early Yield (%) 2000 | Early Yield (T/ha) 2000 |
|---|---|---|---|---|
| 'Moutere' | 40.5 | 6.3 | 31.1 | 6.5 |
| 'Haida' | 23.7 | 5.2 | | |
| 'Qualicum' | 28.5 | 4.5 | 20.3 | 3.2 |
| 'Chilliwack' | 30.3 | 3.8 | 23.6 | 2.5 |
| 'Tulameen' | 18.5 | 2.7 | 15.5 | 3.7 |
| 'Malahat' | 37.5 | 6.8 | 47.3 | 6.2 |

Table 2. shows the figures for percentage early production and the quantity of early production of Moutere (British Columbia), compared with the parent cultivars Haida and Qualicum. A comparison is also made with Chilliwack and Tulameen, two high quality fresh market cultivars from the British Columbia programme, and Malahat, the early, fresh market cultivar from the British Columbia programme. Moutere is clearly superior for early production to all cultivars other than Malahat in these trials.

BRIEF DESCRIPTION OF THE DRAWINGS

The accompanying photographs show typical specimens of the new variety in color as true as is reasonably possible. The photographs were prepared in July 2001 and depict three year-old plants and plant parts grown outdoors at Canada Agriculture, Abbotsford, British Columbia, Canada.

DETAILED DESCRIPTION

Figure 1:
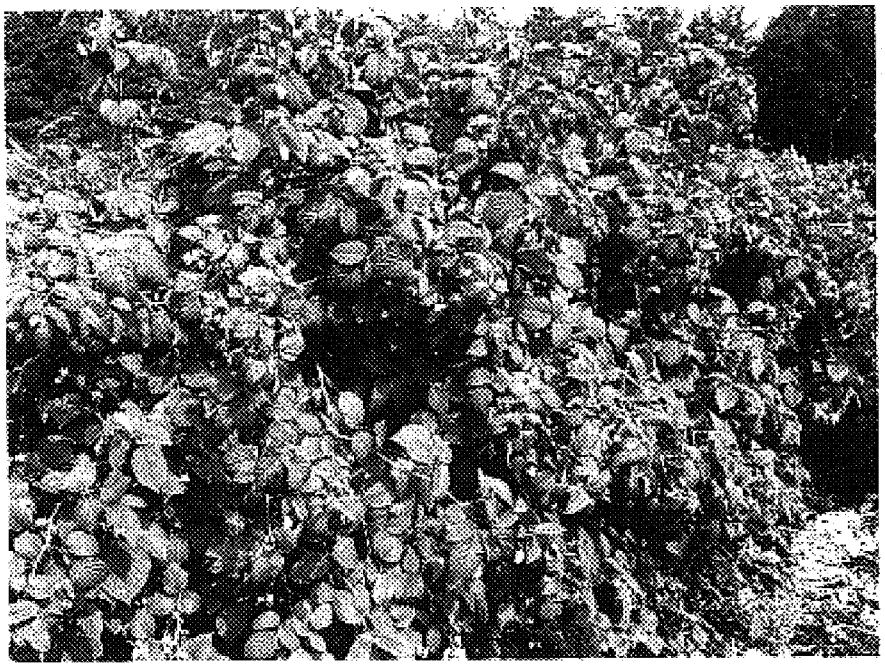
FIG. 1. Illustrates a fruiting plant of the variety showing the large fruit size and high productivity. The fruiting trusses are shown to be medium long length and productive.

Horticultural terminology is used in accordance with UPOV guidelines for raspberry. All dimensions in millimeters, weights in grams (unless otherwise stated). Where a color reference is given these refer to The R.H.S. Colour Chart, The Royal Horticultural Society, London. 4$^{th}$ Edition, 2001. The specimens described were grown at HortResearch Nelson, New Zealand and Agriculture Canada at Abbotsford in British Columbia, Canada. The plants were 2–4 years old in the 1999–2001 seasons when the observations were made.

Environmental data for the New Zealand growing area demonstrates conditions in spring and early summer (equating to the harvest period for the variety) as follows:

Spring (September/October); mean daily temperature in the range 10–12° C. (mean daily minimum 5.8° C., mean daily maximum 16.5° C.).

Early summer (December/January); mean daily temperature 16.8° C. (mean daily minimum 11.1° C., mean daily maximum 22.4° C.).

A cool temperate area, frost conditions are typically experienced in winter, with the lowest winter air temperature unlikely to be colder than −6° C. Average annual rainfall is approximately 1125 mm.

Environmental data for the Abbotsford, British Columbia, Canada growing area demonstrates conditions in spring and early summer (equating to the harvest period for the variety) as follows:

Spring (April/May); mean daily temperature in the range 10–11° C. (mean daily minimum 5.5° C., mean daily maximum 15.5° C.).

Early summer (June/July); mean daily temperature 16° C. (mean daily minimum 10° C., mean daily maximum 21.5° C.).

In winter temperatures below 0° C. are common, the daily mean for December/January is 2.5° C. with the lowest temperature unlikely to be colder than −13° C. Average annual rainfall is approximately 1500 mm.

Figure 2:
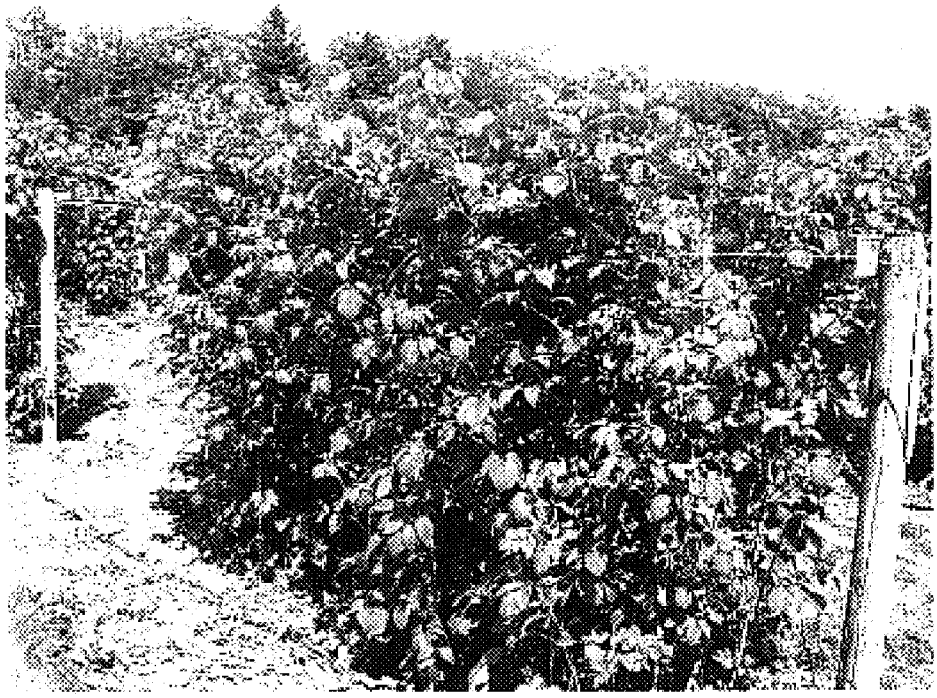
FIG. 2. Illustrates typical plants of the variety showing the upright nature of the canes at full canopy development FIG. 3. Illustrates enlarged close-up side and end views of typical fruit of the variety, photographed on a 1 cm×1 cm grid.
Figure 7:
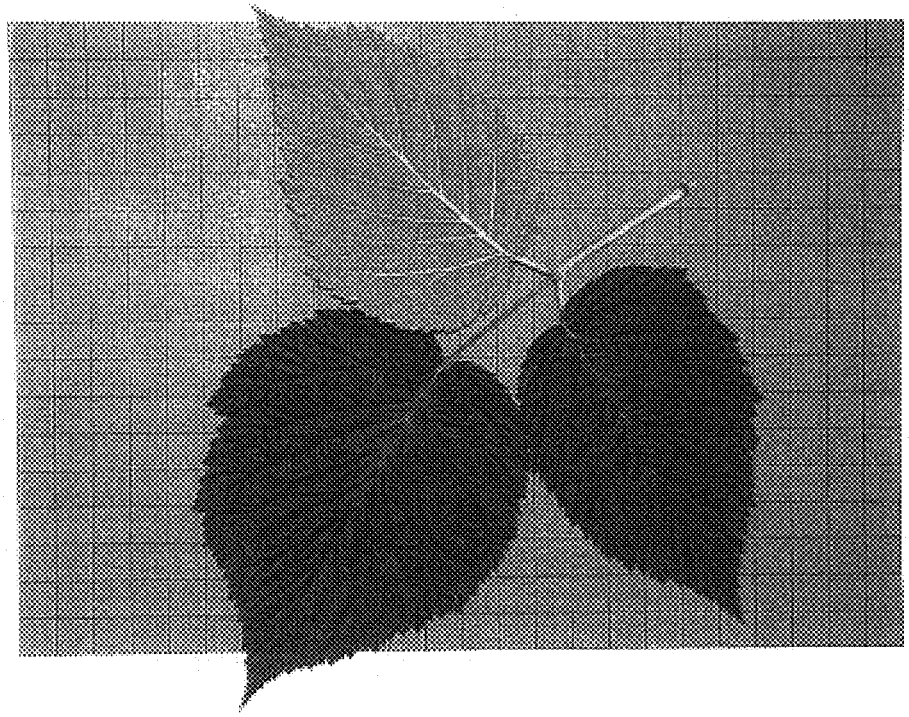
Figure 8:
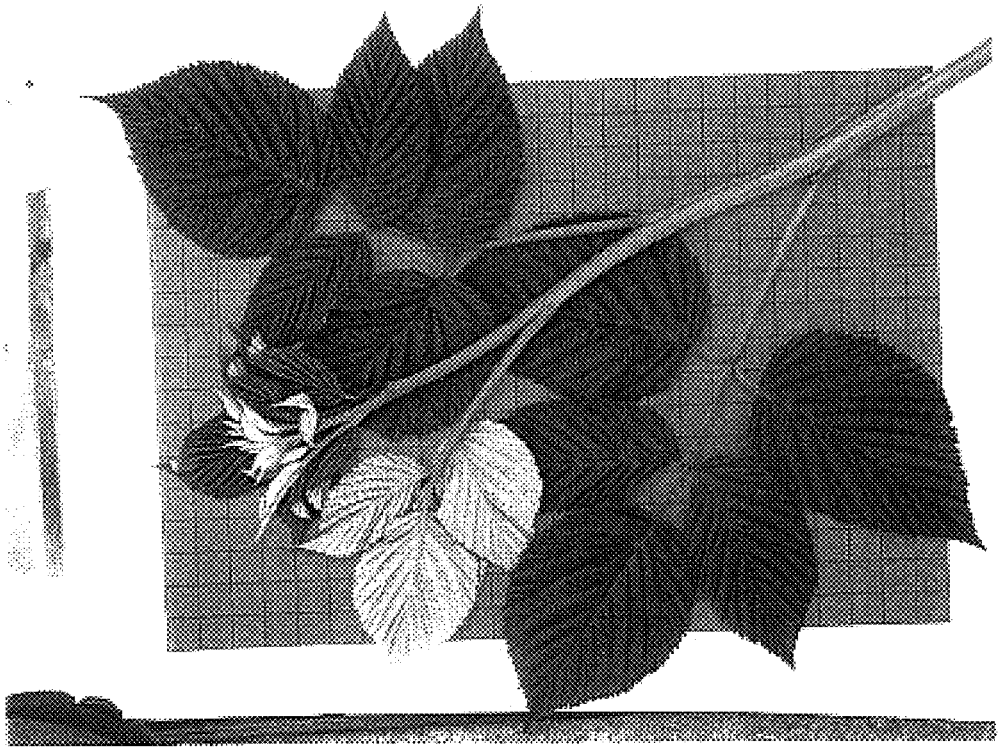
FIG. 8. Illustrates a primocane tip of the variety showing the upper and lower surface of the leaves.

Plant and foliage: The plant exhibits an upright growth habit (FIG. 2). Strong vigor is exhibited and mature plant height is commonly in the range 1500 mm to 2200 mm, although this may vary with the growing conditions. There are typically 30 nodes per cane, with an internode length in the range 60–80 mm. Spines (prickles/thorns) are sparse, particularly on the upper cane section and are very small on mature canes (typically 7–12 spines occur along a cane length of 1–1.5 m, spines average 0.9 mm long at the base and 0.4 mm high), but may be denser and longer on juvenile canes. Spines are very tapered, acicular in shape and near Purple N79A in color. Canes are upright and are typically show light brown-tan coloration (near Greyed-orange 175A) in winter. Some purple coloration (near Red-purple 59A) is evident on the sunny side of the cane. The fruit is borne primarily on the previous year's growth. The fruiting trusses are medium long in length, commonly measuring 500–700 mm, and are weakly ascending, but are hanging when fruit has ripened. Fruit presentation at harvest time is excellent and well suited to hand-picking. The leaves of primocanes are compound, moderately crinkled, flat and moderately dull, with strong silver coloration on the leaf underside. (FIGS. 7 and 8). The number of leaflets per internode is predominantly five. The base of the leaflet is ovate in shape and leaflets typically average 52 mm in diameter and 91 mm in length. The coloration of the upper surface of the leaf is green (near Green 137A), the under side being markedly lighter in coloration (near Greyed-green 191C). While the leaves do not have distinguished marginal or vein coloration, the venation has noticeable rises and falls. The leaf petiole typically averages approximately 85 mm in length and 2.6 mm in diameter. It is near Yellow-green N144D in color, with some anthocyanin coloration observed (near Red-purple 59A). Young shoots are semi-erect and are near Yellow-green 144A in color.

Inflorescence: Flowers are numerous and borne on a racemose inflorescence that consists of a lateral or truss giving rise to numerous slender pedicels and occasionally a peduncle giving rise to two or more pedicels. Flowers are white and pedicels have few–medium spines (thorns/ prickles). At HortResearch Nelson, New Zealand the date bud burst commences is approximately 2$^{nd}$ September, with fifty percent of buds burst by mid September (approximately 15$^{th}$ September). The time of bloom is mid season for a summer-fruiting raspberry, with peak flowering early-mid November. Typically there are five petals, elongated ovate in shape with a rounded apex and flat base. The petals average approximately 6.7 mm in length and 2.7 mm in width. They are typically smooth in texture, have a smooth margin and are near White 155C in color. The pedicel length averages approximately 20.0 mm long. However, the more basal the pedicel the longer it commonly becomes with pedicel lengths up to about 50 mm being observed. The pedicel averages approximately 0.6 mm in diameter and is near Yellow-green 144A in color. A typical flower diameter is approximately 27 mm (from sepal tip to sepal tip i.e. the widest part of the flower). The flowers have no discernible fragrance. Five sepals that together make up the calyx are present. These are green in coloration (near Yellow-green 145B) and measure approximately 10.5 mm in length from base to tip. The calyx vertically surrounds the flower when it is shut, but is opened out and lies horizontal when the flower is fully open, then as fruit ripens it folds back toward the pedicel thereby fully exposing the fruit. The druplets that together make up the berry form on a large receptacle which remains attached to the plant after fruit is removed. At harvest the receptacle is conical in shape, tapered and typically 20 mm long. The reproductive organs are typical for flowers of *Rubus idaeus* L.; the stigmas average approximately 150 in number and are near Green-white 157A in color; there are approximately 100–110 anthers, these being brown (depending on maturity) near Grey-brown 199A in color; the filaments averaging approximately 4.7 mm in length and being near White 155C in color.

Harvest: At HortResearch Nelson, New Zealand, the typical start date for picking the new variety is 10$^{th}$ December. Fifty percent of the harvest is typically completed by 22$^{nd}$ December, and harvest ceases approximately 4$^{th}$ January. At Abbotsford in British Columbia, the typical start date for picking the new variety is 7$^{th}$ July. Fifty 50 percent of the harvest is typically completed by 19$^{th}$ July, and harvest ceases approximately 31$^{st}$ July. In British Columbia the date at which 50 percent of the Moutere harvest is complete is approximately one day later than for 'Malahat' and three layers than both Qualicum and Tulameen. However, the duration of the harvest period for 'Moutere' is eight days shorter than 'Malahat', two days shorter than Qualicum and ten days shorter than Tulameen.

At harvest 'Moutere' fruit remain firmly attached to the receptacle and moderately strong force is required to dislodge the berry from the receptacle. Because of this adherence fruit are not suitable for harvest by machine. 'Moutere' is recommended for early season production for fresh market fruit and it may also be suitable for long cane production.

Figure 3:
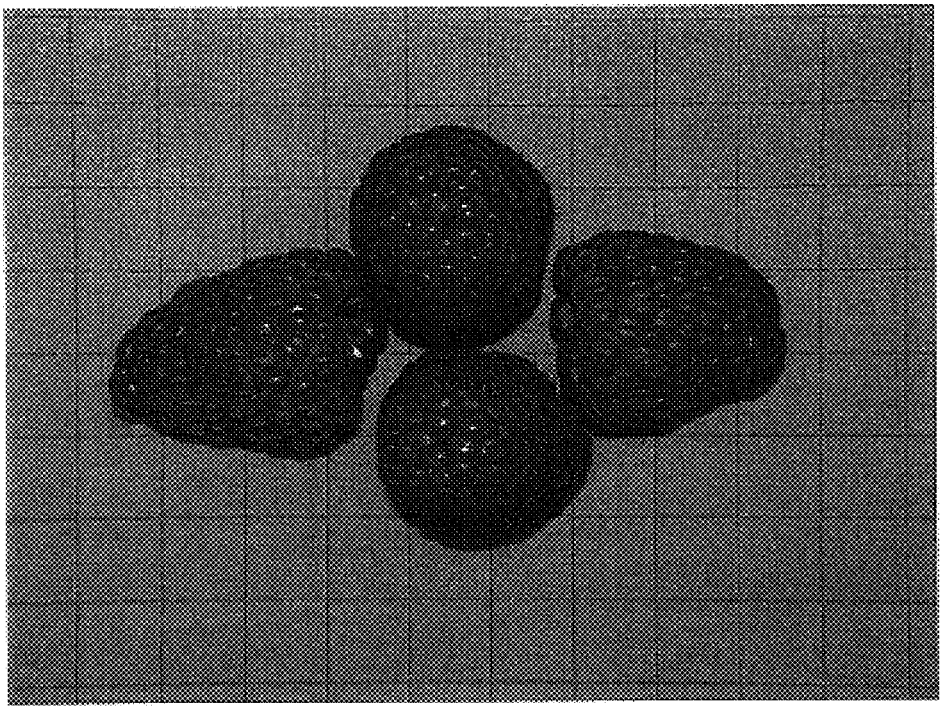
Figure 4:
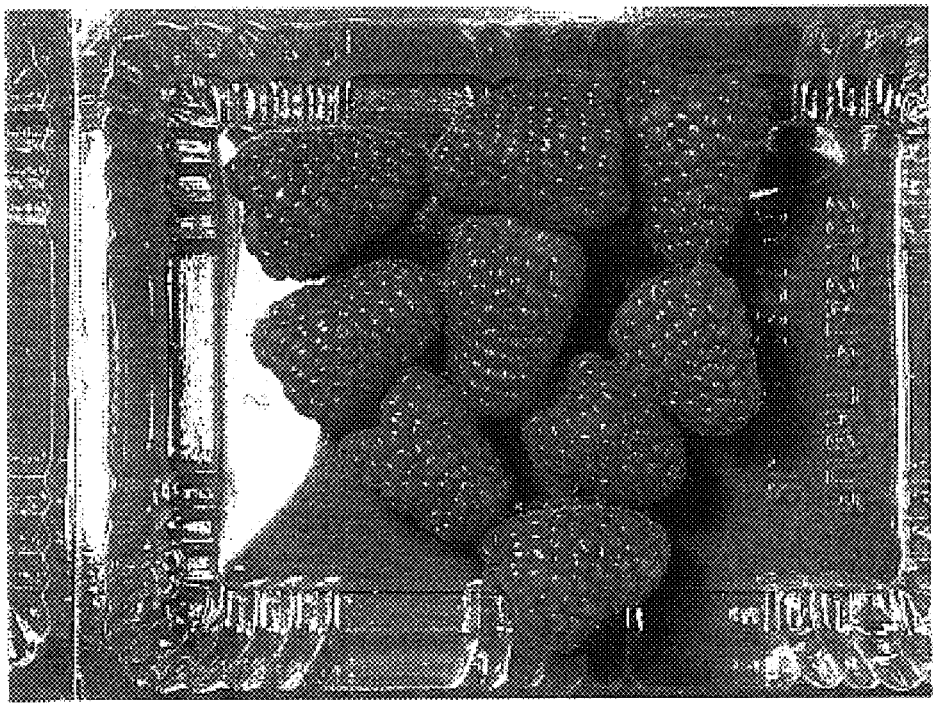
FIG. 4. Illustrates enlarged close-up views of typical fruit of the variety
Figure 5:
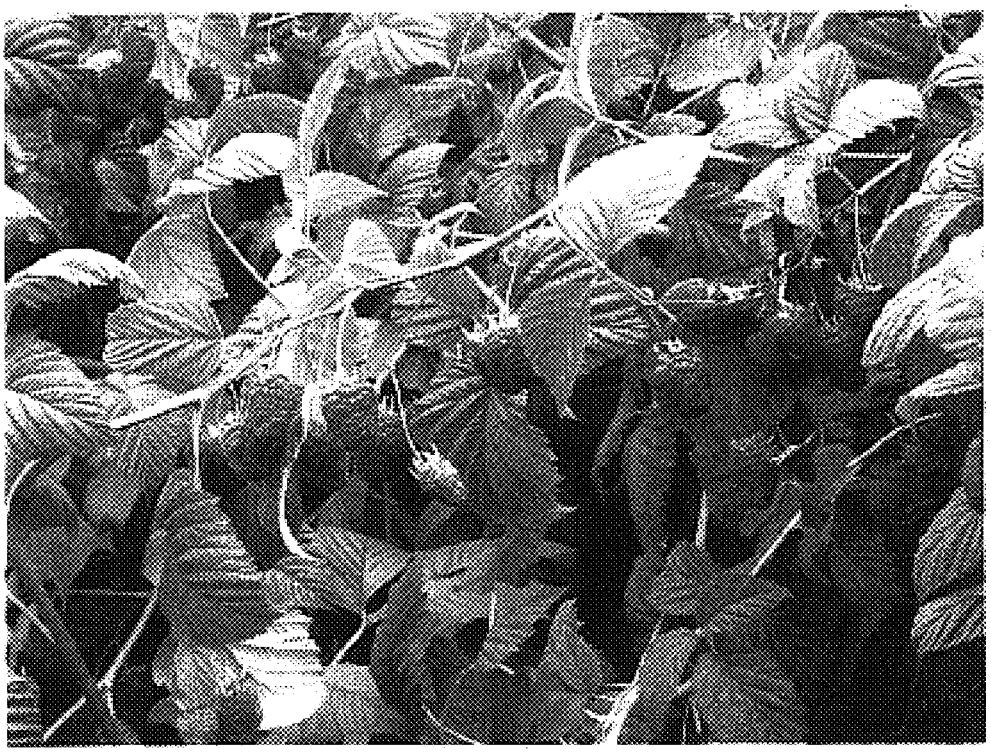
FIG. 5. Illustrates a close up view of fruit on the plant
Figure 6:
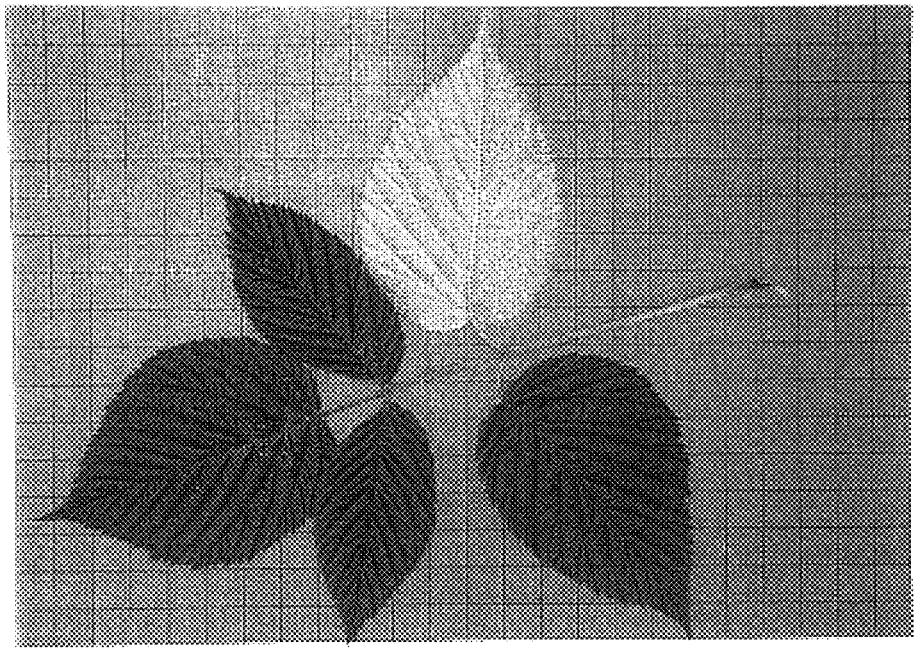
FIGS. 6 and 7. Illustrate primocane and floricane leaves of the variety showing both upper and lower leaf surfaces.

Fruit: The berries formed on 'Moutere' are large in size. Average weight of berries produced in British Columbia during the 1999 summer was 4.6 g and berries are typically on average 25 mm long and 21 mm wide at the widest point with a hollow center measuring 14 mm. The fruit is long-conical in configuration (FIG. 3) and is bright red in appearance (external color near Red-purple 59A, internal color near Red 53A), with a high level of glossiness. The berries are firm and of medium raspberry flavor. Percentage rotten fruit harvested in British Columbia was 1.8% in 1999 and 4.5% in 2000 compared with 'Meeker' (1.6%, 1.9%), 'Malahat' (1.2%, 1.6%), 'Qualicum' (1.5%, 4.4%) and 'Tulameen' (2.4%, 4.6%). The seeds average 2.5 mm long and 1.3 mm wide, and are near Greyed-orange N170D in color when dry. Seed numbers per fruit average 148 and weigh individually on average 1.5 mg.

Shelf life trials in British Columbia 1999 showed 'Moutere' had 13.9% of fruit infected with Botrytis, after 48 hours at ambient temperatures. Two further trials in 2000 showed 7.9% and 45.8% fruit rotted after 48 hours, respectively. Comparative data for 'Meeker' was 28.9% (1999) and 26.6%, 70.3%, 49.6% (three separate trials in 2000), 'Malahat' (18.9%, 20.3%, 71.9%, 34.8%), 'Qualicum' (17.8%, 3.2%, 46.9%, 53.1%) and 'Tulameen' (25.6%, 15.6%, 87.5%, 62.5%).

Pest and disease resistance: Resistance to aphids is unknown. Since the selection of this clone in 1989–90 numerous tests for raspberry bushy dwarf virus (RBDV) have been done on 'Moutere' in New Zealand and in British Columbia using ELISA, but on no occasion has the virus been detected in spite of high infection pressure. From this we suggest that 'Moutere' is likely to be resistant to the common strain of RBDV found in New Zealand and the Pacific Northwest.

Cultivation: 'Moutere' performs well in the cool temperate climate of the Nelson region under standard management practices for commercial raspberry production. Initial indications are that 'Moutere' also performs well in USA Hardiness zones 8–10.

I claim:

1. A new and distinct variety of raspberry plant named 'Moutere', substantially as herein illustrated and described.

* * * * *